United States Patent [19]

Fujino et al.

[11] 4,206,199

[45] Jun. 3, 1980

[54] NOVEL GLUCAGON FRAGMENT AND ITS DERIVATIVES

[75] Inventors: Masahiko Fujino; Mitsuhiro Wakimasu, both of Takarazuka; Akira Ohneda, Sendai, all of Japan

[73] Assignee: Takeda Chemical Industries, Ltd., Osaka, Japan

[21] Appl. No.: 924,553

[22] Filed: Jul. 14, 1978

[30] Foreign Application Priority Data

Jul. 22, 1977 [JP] Japan .................................. 52-88556
Sep. 21, 1977 [JP] Japan .................................. 52-114242

[51] Int. Cl.² ..................... A61K 39/00; A61K 37/00; C07C 103/52
[52] U.S. Cl. ..................................... 424/85; 424/177; 260/112.5 R
[58] Field of Search ................. 260/112.5 R; 424/177, 424/85

[56] References Cited

U.S. PATENT DOCUMENTS 3,642,763  2/1972  Wunsch et al. ............... 260/112.5 R

*Primary Examiner*—Delbert R. Phillips
*Attorney, Agent, or Firm*—Stevens, Davis, Miller & Mosher

[57] ABSTRACT

(a) A novel glucagon fragment (15–29) of the formula:

H-Asp-Ser-Arg-Arg-Ala-Gln-Asp-Phe-Val-Gln-Trp-Leu-Met-Asn-Thr-OH, (b) a novel product obtained by conjugating the glucagon fragment (15–29) with bovine serum albumin by means of glutalaldehyde,
(c) a novel antibody specifically reactive to pancreatic glucagon produced by administering to a mammalian animal the product of the above (b), and
(d) a novel peptide of the formula

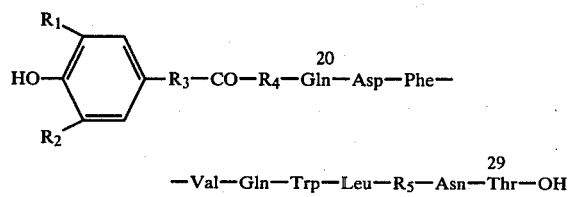

wherein $R_1$ and $R_2$ respectively mean H or radioactive I, $R_3$ is an alkane residue having up to 4 carbon atoms which may optionally have $NH_2$ or OH, $R_4$ is a peptide fragment corresponding to the 1 to 5 amino acid residues ending with the 19-alanyl of pancreatic glucagon, and $R_5$ is Met or Nle, being efficiently useful for estimation by radioimmunoassay of pancreatic glucagon levels in blood together with the antibody of the above (c).

4 Claims, No Drawings

NOVEL GLUCAGON FRAGMENT AND ITS DERIVATIVES

This invention relates to a novel glucagon fragment which is useful as antigen for producing an antibody highly reactive specifically to pancreatic glucagon and also relates to novel derivatives of the glucagon fragment which are useful for estimation by radioimmunoassay of blood levels of pancreatic glucagon.

Glucagon is a hormone which plays a very important role in the glucose metabolisms of animals and, clinically, it is important to estimate its concentration in the blood.

Glucagon exists in two forms which are said to be structurally similar, namely pancreatic glucagon

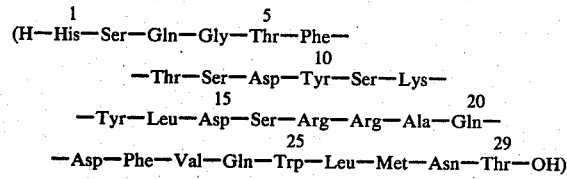

and gut glucagon, and the one which mainly influences the blood glucose level is said to be pancreatic glucagon. While data clinically required is thus chiefly the blood concentration of pancreatic glucagon, it is well known that the production of an antibody by means of the conjugate of available pancreatic glucagon with bovine serum albumin rarely yields a clinically useful antibody specific to pancreatic glucagon but mainly gives an antibody crossreactive with both pancreatic and gut glucagons. In order to produce an antigen which may be used in the production of an antibody specific to pancreatic glucagon, we synthesized a number of different peptides and investigated their characteristics. The research led us to the surprising discovery that a pentadecapeptide corresponding to the fragment from the amino acid residue in 15-position through the C-terminal of glucagon is very useful for the above purpose. The instant invention has been conceived and developed on the above finding.

This invention is primarily directed to the following aspects:

(a) a novel glucagon fragment (15–29) of the formula:

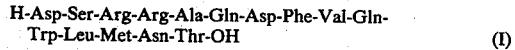

(b) a novel product prepared by conjugating the glucagon fragment (15–29) of the above (a) with bovine serum albumin by means of glutalaldehyde, (c) a novel antibody specifically reactive to pancreatic glucagon, which is produced by administering to a mammalian animal the product of the above (b), and (d) a novel peptide of the formula Whenever the amino acids, peptides, protective groups, active groups, etc. are designated by abbreviations in this specification, such abbreviations are used in conformity with the nomenclature adopted by IUPAC-IUB Commission on Biological Nomenclature or the common terminology in the field of art. The following is a partial list of such abbreviations. It should be understood that where amino acids, etc. have optical isomers, they represent L-isomers unless otherwise specified.

Arg: Arginine
Trp: Tryptophan
Asn: Asparagine
Asp: Aspartic acid
Thr: Threonine
Ser: Serine
Glu: Glutamic acid
Gln: Glutamine
Ala: Alanine
Val: Valine
Met: Methionine
Met(O): Methionine sulfoxide
Leu: Leucine
Nle: Norleucine
Phe: Phenylalanine
Z: Carbobenzoxy
Boc: t-Butyloxycarbonyl
OBu$^t$: t-Butyl ester
OBzl: Benzyl ester
ONB: N-hydroxy-5-norbornene-2,3-dicarboximide ester
MBS: p-Methoxybenzenesulfonyl
HONB: N-hydroxy-5-norbornene-2,3-dicarboximide
DCC: N,N'-dicyclohexylcarbodiimide
DCU: N,N'-dicyclohexylurea
DMF: N,N-dimethylformamide
NMP: N-methyl-2-pyrrolidone
TFA: Trifluoroacetic acid
THF: Tetrahydrofuran
TEA: Triethylamine
DCHA: Dicyclohexylamine
CMC: Carboxymethyl-cellulose
BSA: Bovine serum albumin
Hpa: p-Hydroxyphenylacetic acid
Hpp: p-Hydroxyphenylpropionic acid The peptide (I) according to this invention can be produced by procedures which are commonly employed in the art of peptide synthesis. Thus, both the solid-phase and the liquid-phase methods of synthesis can be employed, although liquid phase synthesis is advantageous in many instances. Such methods for peptide synthesis have been described, for example in Schröder and Lübke: "The Peptides", Vol. 1 (1966), Academic Press, New York, U.S.A. and Neurath and Hill "The Proteins", Vol. 2 (1976), Academic Press, New York, U.S.A. Thus, there may be mentioned the azide process, acid chloride process, acid anhydride

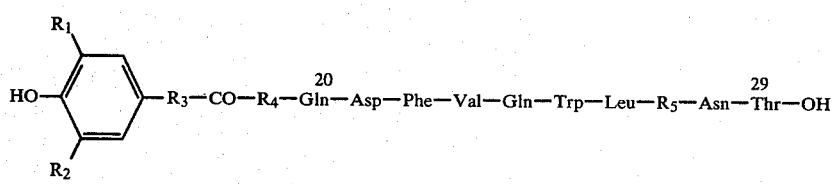

process, mixed acid anhydride process, DCC process, active ester process, the process involving the use of Woodward's Reagent K, carbodiimidazole process, redox process, DCC/Additive (e.g. HONB, HOBt, HOSu) process, etc.

(a) Glucagon fragment (15-29)

The compound (I) according to this invention can be produced by condensing a starting material having a reactive carboxyl group, which corresponds to either one of the two fragments of (i) as divided at an optional one of the peptide-linkages, with a mating starting material having a reactive amino group, which corresponds to the other of said two fragments, in a manner conventional per se and, if the resulting condensation product carries a protective group or protective groups, removing such protective group or groups in a manner conventional per se.

In carrying out the reaction for the production of peptide (I), it is normally preferable that Asp be previously protected. In many cases, the contemplated product (I) is obtained on removal, in the final step, of protective groups from peptide (I) as protected in at least one of the constituent amino acid residues of peptide (I). The protection of functional groups which should not be involved in the reaction and which may be present in starting materials, the protective groups useful for the purpose, the removal of such protective groups, the activation of functional groups to be involved in the reaction, etc. may be carried out in manners conventional per se or be selected from among the known groups.

As examples of the amino-protecting groups useful for the protection of amino groups in the starting materials, there may be mentioned carbobenzoxy, t-butyloxycarbonyl, t-amyloxycarbonyl, isobornyloxycarbonyl, p-methoxybenzyloxycarbonyl, 2-chlorobenzyloxycarbonyl, admantyloxycarbonyl, trifluoroacetyl, phthalyl, formyl, o-nitrophenylsulfenyl, diphenylphosphinothioyl, etc. As examples of carboxyl-protecting groups, there may be mentioned such ester-forming groups as those capable of giving alkyl esters (e.g. methyl, ethyl, propyl, butyl, t-butyl, etc. esters), benzyl ester, p-nitrobenzyl ester, p-methoxybenzyl ester, p-chlorobenzyl ester, benzhydryl ester, etc. and hydrazide-forming groups such as those capable of giving carbobenzoxy hydrazide, t-butyloxy-carbonyl hydrazide, trityl hydrazide, etc.

As groups for protecting the guanidino group of arginine, there may be mentioned nitro, tosyl, p-methoxybenzenesulfonyl, carbobenzoxy, isobornyloxycarbonyl, admantyloxycarbonyl, etc. The guanidino group may also be protected in the form of a salt with an acid (e.g. benzenesulfonic acid, toluenesulfonic acid, hydrochloric acid, sulfuric acid, etc.)

The hydroxyl group of threonine may be protected, for example by way of known esterification or etherification. As examples of groups suitable for said esterification, there may be mentioned lower alkanoyl groups (e.g. acetyl), aroyl groups (e.g. benzoyl), and groups derived from carbonic acid, such as benzyloxycarbonyl, ethyloxycarbonyl, etc. As groups suitable for said etherification, there may be mentioned benzyl, tetrahydropyranyl, t-butyl, etc. The hydroxyl group of threonine, however, need not necessarily be protected. Methionine may be previously protected in the form of a sulfoxide. As examples of the activated carboxyl group in the starting material, there may be mentioned the corresponding acid anhydride, azide, active ester (e.g. esters with pentachlorophenol, p-nitrophenol, N-hydroxysuccinimide, N-hydroxybenzotriazole, N-hydroxy-5-norbornene-2,3-dicarboximide, etc.). Some reactions for the formation of peptide bonds may be conducted in the presence of a dehydrating agent (such as carbodiimide reagents, e.g. dicyclohexylcarbodiimide; carbodiimidazole, etc.). The condensation reaction for the production of the contemplated peptide (I) of this invention can be carried out in the presence of a solvent. The solvent may be selected from among the solvents which are known to be useful for the purpose of peptide-forming condensation reactions. Thus, for example, dry or aqueous dimethylformamide, dimethylsulfoxide, pyridine, chloroform, dioxane, dichloromethane, tetrahydrofuran, ethyl acetate, N-methylpyrrolidone, etc. as well as suitable mixtures thereof may be mentioned.

The reaction temperature may be selected from the range known to be useful for the purpose of peptide-forming condensation reactions. Thus, it may normally be within the range of about $-40°$ C. to about $60°$ C. and, preferably, about $-20°$ C. to about $0°$ C.

After the condensation reaction, any protective group or groups that may exist on the product peptide (I) can be removed by conventional procedures. As examples of such known procedures, there may be mentioned reductive procedures (e.g. hydrogenation with a catalyst such as palladium black, reduction with sodium metal in liquid ammonia), acidolysis (e.g. acidolysis with a strong acid such as trifluoroacetic acid, hydrogen fluoride, methanesulfonic acid, etc.) and so forth.

The peptide (I) produced in the above manner can be isolated from the reaction mixture by known peptide-separation procedures (e.g. extraction, distribution, column chromatography, etc.).

Since the peptide (I) contains arginine residues, it may be isolated in the form of a salt. As examples of acids capable of forming such salts, there may be mentioned inorganic acids such as hydrochloric acid, hydrobromic acid, nitric acid, sulfuric acid, phosphoric acid, etc. and organic acids such as formic acid, acetic acid, propionic acid, lactic acid, citric acid, oxalic acid, maleic acid, etc.

The starting materials for the production of the peptide (I) of this invention can also be prepared by the above-mentioned conventional procedures for peptide synthesis, i.e. by condensing amino acids in accordance with the amino acid sequence of each starting material.

(b) conjugate of the glucagon fragment (15-29) with bovine serum albumin by means of glutalaldehyde, and

(c) a novel antibody specifically reactive to pancreatic glucagon

The conjugation of the pentadecapeptide (I) thus obtained with bovine serum albumin can be carried out by the known glutaldehyde process [e.g. M. Reichlin, J. J. Schnure, and K. Vance, "Proceedings of The Society for Experimental Biology and Medicine 128, 347–350 (1968)"]. Bovine serum albumin is used as the antigen carrier and, in some cases, may be replaced with other proteins useful for the purpose. The optimal ratio of the glucagon fragment (I) to bovine serum albumin is 10 mg to about 20 mg and, in many instances, satisfactory results are obtained when the reaction pH is somewhere in the neighborhood of 7.3. While, in many cases, a reaction time of 2 to 6 hours is adequate at room temperature, a reaction time of about 3 hours will often prove particularly beneficial.

The conjugate thus obtained can be dialyzed against water at about 4° C. and lyophilized for storage purposes in the known manner.

This conjugate according to this invention is capable of producing an antibody which is highly reactive and specific to pancreatic glucagon with efficiency when administered to a mammalian animal (e.g. rabbit, mouse) in a manner conventional per se. The glucagon fragment (I) may be used in a barely sufficient amount for antibody production and, in some instances, five subcutaneous administrations of about 2 mg each at intervals of 2 weeks may produce the antibody. Thus, the antibody is formed in situ in the mammal to be treated.

(d) A novel peptide (II)

It is well known that estimation of blood levels of pancreatic glucagon by radioimmunoassay requires the use of not only an antibody reactive specifically to pancreatic glucagon but also hormone iodinated with radioactive $^{125}I$ or $^{131}I$ which is also reactive specifically to the antibody.

In known radioimmunoassay for estimation of blood levels of pancreatic glucagon, iodoglucagon is used. The iodo-glucagon, however, tends to react with non-specific antibodies crossreactive to gut glucagon and pancreatic glucagon. It is, thus, well knwon that a selective estimation of pancreatic glucagon alone is a difficult task.

The research undertaken by us for the purpose of producing an I-labeled compound reactive specifically with antibodies specific to pancreatic glucagon led to the surprising discovery that a peptide of the formula

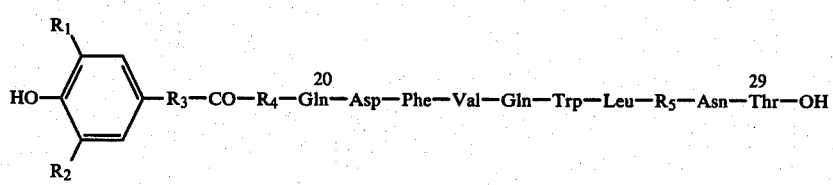
(II)

($R_1$ and $R_2$, respectively, represent H or radioactive I; $R_3$ is an alkane residue of up to 4 carbon atoms which may optionally have $NH_2$ or OH; $R_4$ is a peptide fragment corresponding to the 1 to 5 amino acid residues ending with 19-alanyl of pancreatic glucagon; $R_5$ represents Met or Nle)
reacts specifically with antibodies specific to pancreatic glucagon, and
that a peptide of the formula (II'):

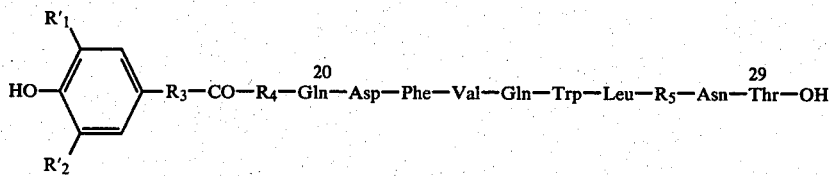
(II')

(wherein $R'_1$ and $R'_2$ are such that either one of them is radioactive I with the other being H or both of them are respectively radioactive I; $R_3$ is an alkane residue of up to 4 carbon atoms which may optionally have $NH_2$ or OH; $R_4$ is a peptide fragment corresponding to the 1 to 5 amino acid residues ending with 19-alanyl of pancreatic glucagon; $R_5$ represents Met or Nle)
is of great value as a diagnostic agent for the radioimmunoassay of pancreatic glucagon. The findings were followed by further research which has culminated in this instant invention.

This invention is, therefore, directed to the peptide (II) and a diagnostic agent containing the peptide (II') which is useful for the radioimmunoassay of pancreatic glucagon.

The radioactive iodine as represented by $R_1$, $R_1'$, $R_2$ and $R_2'$, respectively, may for example be $^{125}I$ or $^{131}I$.

As examples of said alkane residue of up to 4 carbon atoms, which is designated by $R_3$, there may be mentioned $-CH_2-$, $-CH_2CH_2-$, $-CH_2CH_2CH_2-$, $-CH_2CH_2CH_2CH_2-$ and so forth. These alkane residues may optionally have $NH_2$ or OH. Where the N-terminal amino acid residue of peptide (II) is tyrosyl, it may be any of the l-, d- and racemic forms.

$R_4$ represents a peptide fragment corresponding to the 1 to 5 amino acid residues ending with 19-alanyl of pancreatic glucagon, thus meaning $$\overset{19}{Ala}, \overset{18}{Arg}-\overset{19}{Ala}, \overset{17}{Arg}-\overset{18}{Arg}-\overset{19}{Ala},$$
$$\overset{16}{Ser}-\overset{17}{Arg}-\overset{18}{Arg}-\overset{19}{Ala} \text{ or } \overset{15}{Asp}-\overset{16}{Ser}-\overset{17}{Arg}-\overset{18}{Arg}-\overset{19}{Ala}.$$

The peptide (II) according to this invention can be produced by the procedures per se established for peptide synthesis as mentioned before for the preparation of the glucagon fragment (I).

In many instances, the peptide (II') can be advantageously produced by iodinating the peptide (II) where $R_1=R_2=H$ with radioactive iodine in a manner conventional per se.

In the production of peptide (II), it is normally often preferable that Asp be previously protected. The final reaction step, in certain cases, comprises removing the protective group or groups from the protected peptide (II), i.e. the peptide (II) with at least one of its constituent amino acid residues having been protected, and, in other instances, comprises introducing the group of the formula

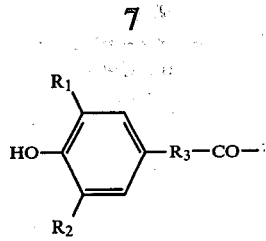

into the remainder of the peptide (II) by per se conventional acylation.

The compound (II') may be produced labeling the peptide (II)($R_1=R_2=H$) with radioactive iodine by the conventional chloramine T method [W. M. Hunter and F. C. Greenwood, Nature 194, 495 (1962)].

By selecting a suitable set of reaction conditions, any of the peptide (II') wherein one of $R'_1$ and $R'_2$ is radioactive I with the other being H, the peptide (II') wherein both of $R'_1$ and $R'_2$ are respectively radioactive I, or a mixture in an optional ratio of the mono- and di-iodinated compounds can be obtained. Chloramin T may be employed in a molar ratio of about 1 to 100, preferably about 2 to 60 relative to the peptide (II)($R_1=R_2=H$), for instance. Any of these compounds can be employed in the desired radioimmunoassay. The iodine-labeled peptide (II') may be separated from inorganic iodine by gel-filtration column chromatography on dextran gel (e.g. Sephadex), column chromatography on ion-exchangers (e.g. anion exchangers) or the like and, if desired, may be further lyophilized into powders. The iodinated peptide (II') thus obtained reacts very efficiently with PG-specific antibodies, the intensity of reactions being comparable with that of glucagon.

The glucagon fragment (15–29) and the peptide (II) of this invention have various characteristics, some of which are as follows.

(1) The glucagon fragment (15–29) is capable of producing antibodies highly reactive specifically to pancreatic glucagon in spite of the length of the fragment being half that of glucagon.

(2) The glucagon fragment (15–29) is incapable of producing an antibody reactive to gut glucagon when the fragment is administered to a mammalian animal.

(3) The peptide (II) reacts with PG-specific antibodies derived from various antigens specifically and with efficiency.

(4) The peptide (II') according to this invention is of use in applications where pancreatic glucagon in the blood can be accurately estimated by the radioimmunoassay which is known per se.

In the following examples, thin-layer chromatographic data were obtained by using Silica gel Plate 60 $F_{254}$, (Merck, West Germany) or Cellulose Plate Avicel SF, (Funakoshi Yakuhin K.K., Japan) and the following developer solvent systems.

$Rf^1$ = chloroform-methanol-acetic acid = 9:1:0.5
$Rf^2$ = chloroform-methanol-water = 7:3:0.5
$Rf^3$ = n-butanol-pyridine-acetic acid-water = 30:20:6:24

EXAMPLE 1

(1) Process for the production of Box-Asn-Thr-OBzl

In 300 ml of TFA was dissolved 112 g of Boc-Thr-OBzl and the solution was shaken at room temperature for 20 minutes. To the solution was added 30 ml of concentrated hydrochloric acid and the solution was concentrated under reduced pressure. The residue was dissolved in 1 l of THF and, after cooling with ice, the solution was neutralized with 50 ml of TEA. To this solution was added 76.7 g of Boc-Asn-OH, together with 64.5 g of HONB and 74.3 g of DCC. The mixture was stirred for 15 hours. Following removal of the precipitated byproduct DCU by filtration, the solvent was distilled off under reduced pressure and the residue was dissolved in 1 l of ethyl acetate. The solution was washed with 10% aqueous citric acid (300 ml×3), saturated aqueous sodium hydrogen carbonate (300 ml×3) and water (300 ml×3) in the order mentioned, followed by drying over anhydrous sodium sulfate. The solvent was distilled off under reduced pressure and ether (1 l) was added to the residue. The resultant powder was collected by filtration and recrystallized from acetonitrile. Yield 105.1 g (75.2%); m.p. 165°–166° C.; $[\alpha]_D^{23} -13.9°$ (c=0.9, DMF); $Rf^1$ 0.51;

Elemental analysis: calcd. for $C_{20}H_{29}O_7N_3$—C, 56.75; H, 6.90; N, 9.92; found—C, 57.01; H, 6.89; N, 9.94.

(2) Production of Boc-Met(O)-Asn-Thr-OBzl

To 50.0 g of Boc-Asn-Thr-OBzl was added 170 ml of TFA and the mixture was shaken at room temperature for 30 minutes. The mixture was concentrated and 500 ml of ether was added to the residue. The resultant powder was collected by filtration and dried. The powder was dissolved in 400 ml of THF and, after cooling with ice, 20 ml of TEA was added. Then, Boc-Met(O)-ONB (prepared as follows: 31.3 g of Boc-Met(O).OH and 23.3 g of HONB were dissolved in 200 ml of THF and, after cooling with ice, 26.8 g of DCC was added, followed by stirring for 4 hours) was added to the powder and the mixture was stirred for 15 hours. After the solvent was distilled off under reduced pressure, ethyl acetate (200 ml) and ether (200 ml) were added. The resultant powder was collected by filtration and reprecipitated from acetonitrile. Yield 48.5 g (72.0%); m.p. 145°–147° C.; $[\alpha]_D^{23} -6.5°$ (c=1.1, DMF); $Rf^1$ 0.19;

Elemental analysis: calcd. for $C_{25}H_{38}O_9N_4S$—C, 52.62; H, 6.71; N. 9.82; S. 5.62; found—C, 52.44; H, 6.73; N, 9.60; S, 5.15.

(3) Production of Boc-Leu-Met(O)-Asn-Thr-OBzl

To 15.0 g of Boc-Met(O)-Asn-Thr-OBzl was added 45 ml of TFA and the mixture was shaken at room temperature for 45 minutes. The mixture was concentrated and 100 ml of ether was added. The resultant powder was collected by filtration and dried. This was dissolved in 50 ml of DMF and, after cooling with ice, 5.7 ml of TEA was added. To this solution was added Boc-Leu-ONB (prepared from 6.69 g of Boc-Leu-OH, 5.70 g of HONB and 6.56 g of DCC) and the mixture was stirred for 15 hours. The solvent was distilled off under reduced pressure and 200 ml of ethyl acetate was added to the residue. The resultant powder was collected by filtration and reprecipitated from acetonitrile-ethyl acetate. Yield 15.0 g (83.4%); m.p. 134°–136° C., $[\alpha]_D^{24} -15.1°$ (c=1.0, DMF); $Rf^1$ 0.25;

Elemental analysis: calcd. for $C_{31}H_{49}O_{10}N_5S$—C, 54.45; H, 7.22; N, 10.24; S, 4.69; found—C, 54.62; H, 7.60; N, 9.89; S, 3.95.

(4) Production of Z-Gln-Trp OBzl

In 500 ml of THF was dissolved 50.0 g of H-Trp-OBzl p-toluenesulfonate and, under ice-cooling, 15.4 ml of TEA, 28.0 g of Z-Gln-OH, 19.7 g of HONB and 22.7 g of DCC were added. The mixture was stirred for 15 hours. The precipitated DCU was filtered off, the filtrate was concentrated and the residue was dissolved in 300 ml of ethyl acetate. The solution was washed with saturated aqueous sodium hydrogen carbonate (150 ml×2), 10% aqueous citric acid (150 ml×2) and water (150 ml×2) in the order mentioned. After the solvent was distilled off, the residue was dissolved in 300 ml of THF and the insolubles were filtered off. The filtrate was concentrated and 500 ml of ether was added. The resultant powder was collected by filtration and recrystallized from acetonitrile. Yield 46.1 g (82.8%); $[\alpha]_D^{23}+5.8°$ (c=1.0, DMF); $Rf^1$ 0.60;

Elemental analysis: calcd. for $C_{31}H_{32}O_6N_4$—C, 66.89; H, 5.80; N, 10.07; found—C, 66.79; H, 5.71; N, 10.20.

(5) Production of Z-Val-Gln-Trp-OH

In 700 ml of methanol was dissolved 50.0 g of Z-Gln-Trp-OBzl and catalytic hydrogenation was carried out (catalyst: palladium black) for 5 hours. The resultant crystals were collected by filtration, suspended in 300 ml of DMF and dissolved by addition of 13 ml of TEA. The catalyst was filtered off. To the filtrate was added 37.0 g of Z-Val-ONB and the mixture was stirred for 10 hours, and neutralized with 100 ml of 1 N-hydrochloric acid.

To this solution was added 500 ml of water and the resultant powder was collected by filtration and washed well with methanol. Yield 43.0 g (84.7%); m.p. 246°–247° C.; $[\alpha]_D^{23}+12.4°$ (c=0.9, DMF); $Rf^1$ 0.14;

Elemental analysis: calcd. for $C_{29}H_{35}O_7N_5$—C, 61.58; H, 6.24; N, 12.38; found—C, 61.86; H, 6.30; N, 12.36.

(6) Production of Z-Phe-Val-Gln-Trp-OH

In 100 ml of acetic acid was dissolved 5.1 g of Z-Val-Gln-Trp-OH and catalytic hydrogenation was carried out for 3 hours. The catalyst was filtered off and the filtrate was concentrated. The residue was suspended in 200 ml of DMF, and Z-Phe-ONB (prepared from 2.70 g of Z-Phe-OH) and 2 ml of TEA were added. The mixture was stirred for 7 hours. The solvent was distilled off under reduced pressure and acetic acid-water was added to the residue. The resultant gel was taken by filtration and reprecipitated from methanol. Yield 5.50 g (84.5%); m.p. 240° C.; $[\alpha]_D^{24}+4.1°$ (c=1.0, DMF); $Rf^1$ 0.15;

Elemental analysis: calcd. for $C_{38}H_{44}O_8N_6.\frac{1}{2}H_2O$—C, 63.23; H, 6.28; N, 11.64; found—C, 63.11; H, 6.29; N, 11.80.

(7) Production of Boc-Asp(OBzl)-Phe-Val-Gln-Trp-OH

In a mixture of 150 ml of DMF and 50 ml of acetic acid was dissolved 8.5 g of Z-Phe-Val-Gln-Trp-OH and catalytic hydrogenation was carried out for 5 hours. The catalyst was filtered off and the filtrate was concentrated. To the residue was added 100 ml of methanol and the resultant crystals were collected by filtration and suspended in 200 ml of DMF. To the suspension were added 3.0 ml of TEA and Boc-Asp(OBzl)ONB (prepared from 3.9 g of Boc-Asp(OBzl)-OH, 2.4 g of HONB and 2.7 g of DCC). The mixture was stirred for 10 hours. The solvent was distilled off under reduced pressure and acetic acid-water was added to the residue. The resultant gel was taken by filtration and re-precipitated from DMF-water. Yield 6.3 g (58.1%); m.p. 191°–192° C. (decomp.); $[\alpha]_D^{24}-6.2°$ (c=1.1, DMF); $Rf^1$ 0.11;

Elemental analysis: calcd. for $C_{46}H_{57}O_{11}N_7.3/2-H_2O$—C, 60.64; H, 6.63; N, 10.76; found—C, 60.30; H, 6.48; N, 11.34.

(8) Production of Boc-Gln-Asp(OBzl)-Phe-Val-Gln-Trp-OH

In nitrogen gas streams, 50 ml of TFA was added to 6.0 g of Boc-Asp(OBzl)-Phe-Val-Gln-Trp-OH. The mixture was shaken for 10 minutes and concentrated. To the concentrate was added ether and the resultant powder was collected by filtration and dissolved in 100 ml of DMF. To the solution was added 2.0 ml of TEA, followed by addition of Boc-Gln-ONB (prepared from 1.76 g of Boc-Gln-OH, 1.34 g of HONB and 1.54 g of DCC) and the mixture was stirred for 15 hours. To this mixture was added acetic acid-water and the resultant powder was collected by filtration and reprecipitated from acetonitrile and water. Yield 5.50 g (82.6%); m.p. 210°–212° C. (decomp.); $[\alpha]_D^{24}-10.1°$ (c=1.1, DMF); $Rf^1$ 0.09;

Elemental analysis: calcd. for $C_{51}H_{65}O_{13}N_9$—C, 60.52; H, 6.47; N, 12.46; found—C, 60.19; H, 6.37; N, 12.23.

(9) Production of Z-Arg(MBS)-Ala-OBu$^t$

In 300 ml of methanol was dissolved 31.0 g of Z-Ala-OBu$^t$ and catalytic hydrogenation was carried out for 5 hours. The catalyst was filtered off and the filtrate was concentrated. Separately, 53.0 g of Z-Arg(MBS)-OH.DCHA was suspended in 500 ml of ethyl acetate and the suspension was shaken well with 200 ml of 10% citric acid. It was then rinsed with water, dried over anhydrous sodium sulfate and dissolved in 500 ml of THF. To this solution was added the H-Ala-OBu$^t$ prepared as above, followed by the addition of 14.9 g of HONB. Under ice-cooling, 17.1 g of DCC was added and the mixture was stirred for 10 hours. The precipitated DCU was filtered off and the filtrate was concentrated and dissolved in 500 ml of ethyl acetate. It was then washed with 10% aqueous citric acid (200 ml×3), saturated aqueous sodium hydrogen carbonate (200 ml×3) and water (200 ml×3) in the order mentioned and dried over anhydrous sodium sulfate. The solvent was distilled off under reduced pressure and 300 ml of ether was added to the residue. The resultant powder was collected by filtration. Yield 44.5 g (66.8%); m.p. 126°–127° C.; $[\alpha]_D^{25}-6.0°$ (c=1.0, DMF); $Rf^1$ 0.62;

Elemental analysis: calcd. for $C_{28}H_{39}O_8N_5S$—C, 55.52; H, 6.49; N, 11.56; S, 5.27; found—C, 55.71; H, 6.49; N, 11.81; S, 5.29.

(10) Production of Z-Arg(MBS)-Arg(MBS)-Ala-OBu$^t$

In 500 ml of methanol was dissolved 43 g of Z-Arg(MBS)-Ala-OBu$^t$ and hydrogenation was carried out for 5 hours. The reaction mixture was concentrated and the residue was dissolved in 200 ml of DMF. To the solution were added Z-Arg(MBS)-OH (prepared from 49.7 g of Z-Arg(MBS)-OH.DCHA) and 14.0 g of HONB and, under cooling with ice, 16.1 g of DCC was added. The mixture was stirred for 15 hours. The precipitated DCU was filtered off, the filtrate was concentrated and the residue was dissolved in 500 ml of chloroform. The solution was washed with 10% aqueous citric acid (300 ml×3), saturated aqueous sodium hydrogen carbonate (300 ml×3) and water (300 ml×3) in the order mentioned and dried over magnesium sulfate. The solvent was distilled off under reduced pressure and 300 ml of methanol was added. The resultant crystals were collected by filtration and recrystallized from methanol. Yield 52.4 g (79.2%); m.p. 116°–118° C.; $[\alpha]_D^{25} -8.8°$ (c=1.0, DMF); $Rf^1$ 0.42;

Elemental analysis: calcd. for $C_{41}H_{57}O_{12}N_9S_3 \cdot 2H_2O$—C, 50.86; H, 6.35; N, 13.02; S, 6.62; found—C, 51.05; H, 6.08; N, 13.11; S, 6.62.

(11) Production of Boc-Ser-Arg(MBS)-Arg(MBS)-Ala-OBu$^t$

In a mixture of 80 ml of DMF and 300 ml of methanol was dissolved 30.0 g of Z-Arg(MBS)-Arg(MBS)-Ala-OBu$^t$ and catalytic hydrogenation was carried out for 7 hours. The catalyst was filtered off and the methanol was distilled off under reduced pressure. To the residue were added 7.3 g of Boc-Ser-OH and 6.3 g of HONB. Under ice-cooling, 7.3 g of DCC was added and the mixture was stirred for 10 hours. The precipitated DCU was filtered off, the solvent was distilled off under reduced pressure and the residue was dissolved in 500 ml of chloroform. The solution was washed with saturated aqueous sodium hydrogen carbonate (300 ml×2) and water (300 ml×2), and dried over magnesium sulfate. The solvent was distilled off under reduced pressure and the residue was dissolved in 30 ml of chloroform and applied to a column of silica gel (400 g).

Elution was carried out with chloroform-methanol-acetic acid (9:0.7:0.35) and the fractions from 800 ml through 2 l were pooled, concentrated and treated with ether to obtain a powdery product. Yield 25.5 g (79.0%); m.p. 85°–88° C.; $[\alpha]_D^{26} -20.9°$ (c=1.0, methanol); $Rf^1$ 0.33;

Elemental analysis: calcd. for $C_{41}H_{64}O_{14}N_{10}S_2 \cdot H_2O$—C, 49.09; H, 6.63; N, 13.96; S, 6.39; found—C, 48.96; H, 6.55; N, 13.70; S, 5.84.

(12) Production of Boc-Asp(OBzl)-Ser-Arg(MBS)-Arg(MBS)-Ala-OH

To 10.5 g of Boc-Ser-Arg(MBS)-Arg(MBS)-Ala-OBu$^t$ was added 50 ml of TFA and the mixture was shaken at room temperature for 60 minutes. It was concentrated and treated with 300 ml of ether. The resultant powder was collected by filtration and dissolved in 50 ml of DMF. To this solution were added 4.1 ml of TEA and Boc-Asp(OBzl).ONB (prepared from 3.40 g of Boc-Asp(OBzl).OH, 1.97 g of HONB and 2.27 g of DCC) and the mixture was stirred for 15 hours. The solvent was distilled off under reduced pressure. To the residue was added acetic acid-water and the resultant powder was collected by filtration, dried and reprecipitated from acetonitrile-ether. Yield 6.0 g (51.5%); m.p. 126°–130° C.; $[\alpha]_D^{24} +3.5°$ (c=1.0, DMF); $Rf^1$ 0.17;

Elemental analysis: calcd. for $C_{48}H_{67}O_{17}N_{11}S_2 \cdot 2H_2O$—C, 49.26; H, 6.12; N, 13.17; S, 5.48; found—C, 49.62; H, 5.84; N, 13.00; S, 5.03.

(13) Production of Boc-Gln-Asp(OBzl)-Phe-Val-Gln-Trp-Leu-Met-(O)-Asn-Thr-OBzl To 3.25 g of Boc-Leu-Met(O)-Asn-Thr-OBzl was added 25 ml of TFA and the mixture was shaken at room temperature for 15 minutes. It was then concentrated and the residue was treated with 100 ml of ether. The resultant powder was collected by filtration and dried. The powder was dissolved in 10 ml of NMP and shaken well with 2 ml of TEA, followed by addition of 100 ml of ether. The resultant powder was collected by filtration again and dissolved in 100 ml of DMF. To the solution were added 4.80 g of Boc-Gln-Asp(OBzl)-Phe-Val-Gln-Trp-OH and 2.70 g of HONB. Under ice-cooling, 1.55 g of DCC was added and the mixture was stirred for 58 hours until a gel-like reaction mixture was produced.

The solvent was distilled off under reduced pressure and the residue was washed well with aqueous acetonitrile. Yield 5.75 g (76.8%); m.p. 234° C. (decomp.); $[\alpha]_D^{26} -15.8°$ (c=0.4; acetic acid); $Rf^2$ 0.63;

Elemental analysis; calcd. for $C_{77}H_{104}O_{20}N_{14}S$—C, 58.61; H, 6.64; N, 12.43; S, 2.03; found—C, 59.13; H, 6.96; N, 12.40; S, 1.70.

(14) Production of Boc-Asp(OBzl)-Ser-Arg(MBS)-Arg(MBS)-Ala-Gln-Asp(OBzl)-Phe-Val-Gln-Trp-Leu-Met(O)-Asn-Thr-OBzl To 5.20 g of Boc-Gln-Asp(OBzl)-Phe-Val-Gln-Trp-Leu-Met(O)-Asn-Thr-OBzl was added 1 ml of anisole and, in streams of nitrogen gas, 35 ml of TFA was added. The mixture was stirred at room temperature for 15 minutes and concentrated. The residue was treated with 100 ml of ether and the resultant powder was collected by filtration. The powder was dissolved in 20 ml of NMP and shaken well with 2.77 ml of TEA, followed by addition of 200 ml of ether. The resultant powder was collected by filtration and dissolved in 150 ml of DMF. To this solution were added 3.66 g. of Boc-Asp(OBzl)-Ser-Arg(MBS)-Arg(MBS)-Ala-OH and 2.36 g of HONB. The mixture was cooled to −10° C. with ice-NaCl, followed by addition of 1.02 g of DCC. The reaction mixture was stirred at 0° C. for 10 hours and, then, at room temperature for 24 hours, the precipitated DCU was filtered off. The solvent was distilled off under reduced pressure and 50 ml of water was added to the residue. The powder was collected by filtration and washed well with aqueous acetonitrile. Yield 5.3 g (61.1%); m.p. 237° C. (decomp.); $[\alpha]_D^{26} -7.1°$ (c=0.9, acetic acid); $Rf^2$ 0.63;

Elemental analysis: calcd. for $C_{120}H_{161}O_{34}N_{25}S_3 \cdot 2H_2O$—C, 54.82; H, 6.32; N, 13.32; S, 3.57; found—C, 54.47; H, 6.16; N, 13.07; S, 3.47.

(15) Production of H-Asp-Ser-Arg-Arg-Ala-Gln-Asp-Phe-Val-Gln-Trp-Leu-Met(O)-Asn-Thr-OH To 400 mg of Boc-Asp(OBzl)-Ser-Arg(MBS)-Arg(MBS)-Ala-Gln-Asp(OBzl)-Phe-Val-Gln-Trp-Leu-Met(O)-Asn-Thr-OBzl was added 0.25 ml of anisole. With the addition of 5 ml of methanesulfonic acid, the mixture was shaken at room temperature for 60 minutes. Then, 100 ml of ether was added, whereupon an oily precipitate was produced. The ether was removed by decanting, the residue was dissolved in 10 ml of water and the solution was passed through a column (1×10 cm) of Amberlite IRA-410(acetate-form). The effluent (50 ml) was cooled with ice and stirred with 10 ml of 3N-aqueous ammonia at 0° C. for 30 minutes and lyophilized. The lyophilisate was dissolved in 30 ml of water and run onto a column (2.2×18 cm) of CMC. Elution was carried out by the linear gradient method from water (500 ml) to 0.2 M aqueous ammonium acetate (500 ml). The fractions from 150 ml through 195 ml were pooled and lyophilized. Yield 150 mg. This product was dissolved in 20 ml of water and the solution was run onto a column (1.6×5 cm) of Amberlite XAD-2. Elution was carried out by the linear gradient method from water (200 ml) to 80% ethanol (200 ml) and the fraction from 180 ml through 225 ml were pooled. The ethanol was distilled off and the residue was lyophilized. Yield 115 mg; $[\alpha]_D^{24} -33.6°$ (c=0.6, 50% aqueous acetic acid); $Rf^3$ 0.54(Avicel), amino acid analysis (hydrolysis with 5.7N-HCl containing 4% thioglycolic acid): Arg 2.03(2); Trp 0.87(1); Asp 3.03(3); Thr 0.97(1); Ser 0.73(1); Glu 2.13(2); Ala 1.00(1); Val 1.03(1); Met 1.00(1); Leu1.03(1); Phe 1.03(1) (peptide content 85.7%).

(16) Production of H-Asp-Ser-Arg-Arg-Ala-Gln-Asp-Phe-Val-Gln-Trp-Leu-Met-Asn-Thr-OH[glucagon (15-29)]

In 20 ml of 5% aqueous thioglycolic acid was dissolved 225 mg. of H-Asp-Ser-Arg-Arg-Ala-Gln-Asp-Phe-Val-Gln-Trp-Leu-Met(O)-Asn-Thr-OH and the solution was allowed to stand at 50° C. for 20 hours, whereupon a gel separated. The water was distilled off under reduced pressure and the residue was dissolved in 5 ml of 50% acetic acid. The solution was run onto a column (2.3×118 cm) of Sephadex G-25 and elution was carried out with 50% aqueous acetic acid. The fractions from 180 ml through 240 ml were pooled and lyophilized. Yield 220 mg; $[\alpha]_D^{24} -30.0°$ (c=0.3, 50% aqueous acetic acid); $Rf^3$ 0.59(Avicel); amino acid analysis(hydrolysis with 5.7N-HCl containing 4% thioglycolic acid): Arg 2.15(2); Trp 0.91(1); Asp 3.13(3); Thr 0.99(1); Ser 0.87(1); Glu 2.20(2); Ala 1.05(1); Val 0.96(1); Met 1.00(1); Leu 1.07(1); Phe 1.07(1) (peptide content 79.3%)

EXAMPLE 2

Production of glucagon (15-29)-BSA conjugate

In 4 ml of 0.2 M phosphate buffer (pH 7.3) were dissolved 10 mg of glucagon (15-29) and 20 mg of BSA, followed by the addition of 4 ml of 5% aqueous glutaraldehyde. The mixture was stirred at room temperature for 3 hours, dialyzed (against water, 2 1×4) at 4° C. and lyophilized. Yield 38 mg.

EXAMPLE 3

Production of Antibody

In 1 ml of distilled water was dissolved 8 mg of the conjugate of glucagon (15-29) with BSA (the conjugate of 2 mg of glucagon (15-29) with BSA) prepared in the same manner as Example 2, followed by the addition of 1 ml of Freund complete adjuvant. The components were admixed well to prepare an emulsion and subcutaneously injected into rabbits in several different sites. The above procedure was repeated 5 times at intervals of 2 weeks and, on the 10th day following the last injections, blood samples were taken and a pilot assay was carried out. The result showed that the glucagon antibody was produced that reacted specifically with pancreatic glucagon but did not react with gut glucagon and was usable at the final dilution factor of 63000 times. This antibody did not react with various glucagon fragments [glucagon (15-23) $NH_2$, glucagon (1-14) OMe, glucagon (25-29)].

EXAMPLE 4

(1) Production of HPa-ONB

In 20 ml of THF was dissolved 1.52 g of p-hydroxyphenylacetic acid (Hpa) and, under ice-cooling, 1.97 g of HONB and 2.27 g of DCC were added and the mixture was stirred for 4 hours. Then, the reaction mixture was further stirred at room temperature for 15 hours. The precipitated DCU was filtered off and the solvent was distilled off under reduced pressure. To the residue was added petroleum benzin and the resultant crystals were collected by filtration and recrystallized from ethyl acetate-petroleum benzin. Yield 2.50 g (79.9%); m.p. 137°–138° C.;

Elemental analysis: calcd. for $C_{17}H_{15}O_5N$—C, 65.17; H, 4.82; N, 4.47; found—C, 65.32; H, 4.91; N, 4.75.

(2) Production of Hpa-Asp-Ser-Arg-Arg-Ala-Gln-Asp-Phe-Val-Gln-Trp-Leu-Met-Asn-Thr-OH In a mixture of 5 ml of DMF and 1 ml of water was dissolved 110 mg of H-Asp-Ser-Arg-Arg-Ala-Gln-Asp-Phe-Val-Gln-Trp-Leu-Met-Asn-Thr-OH, followed by the addition of 30 mg of Hpa-ONB. The mixture was stirred for 15 hours, whereby a gel separated out. The solvent was distilled off under reduced pressure and the residue was dissolved in 5 ml of 50% acetic acid. The solution was run onto a column (2.3×118 cm) of Sephadex G-25 and elution was carried out with 50% acetic acid. The fractions from 170 ml to 270 ml were pooled and lyophilized. Yield 105 mg; $[\alpha]_D^{24} +2.6°$ (c=0.55, acetic acid); $Rf^3$ 0.64(Avicel®); amino acid analysis: Arg 2.46(2); Trp 1.02(1); Asp 3.31(3); Thr 0.90(1); Ser 0.79(1); Glu 2.16(2); Ala 0.91(1); Val 1.00(1); Met 1.02(1); Leu 0.98(1); Phe 0.81(1) (peptide content 74%)

EXAMPLE 5

Production of Hpp-Asp-Ser-Arg-Arg-Ala-Gln-Asp-Phe-Val-Gln-Trp-Leu-Met-Asn-Thr-OH In 1 ml of DMF was dissolved 15 mg of p-hydroxyphenylpropionic acid (Hpp) and, under ice-cooling, 20 mg of HONB and 23 mg of DCC were added. The mixture was stirred at that temperature for 15 hours.

Separately, 110 mg of H-Asp-Ser-Arg-Arg-Ala-Gln-Asp-Phe-Val-Gln-Trp-Leu-Met-Asn-Thr-OH was dissolved in a mixture of 5 ml of DMF and 1 ml of water. To this solution was added the DMF solution of Hpp-ONB prepared as above and the mixture was stirred for 15 hours. The solvent was distilled off under reduced pressure, the residue was dissolved in 5 ml of 50% acetic acid and the solution was run onto a column (2.3×118 cm) of Sephadex G-25. Elution was carried out with 50% acetic acid and the fractions from 180 ml to 285 ml were pooled and lyophilized. Yield 100 mg; $[\alpha]_D^{24} +3.0°$ (c=0.50, acetic acid); $Rf^3$ 0.65 (Avicel); amino acid analysis: Arg 2.20(2); Trp 0.95(1); Asp 3.25(3); Thr 1.00(1); Ser 0.82(1); Glu 2.26(2); Ala 1.02(1); Val 1.00(1); Met 1.02(1); Leu 0.99(1); Phe 1.05(1) (peptide content 76.0%)

EXAMPLE 6

Production of H-Tyr-Asp-Ser-Arg-Arg-Ala-Gln-Asp-Phe-Val-Gln-Trp-Leu-Met-Asn-Thr-OH In 1 ml of DMF was dissolved 30 mg of Boc-Tyr-OH and, under ice-cooling, 20 mg of HONB and 23 mg of DCC were added. The mixture was stirred for 15 hours. Separately, 110 mg of H-Asp-Ser-Arg-Arg-Ala-Gln-Asp-Phe-Val-Gln-Trp-Leu-Met-Asn-Thr-Oh was dissolved in a mixture of 5 ml of DMF and 1 ml of water. To this solution was added the DMF solution of the Boc-Tyr-ONB prepared as above and the mixture was stirred for 15 hours. The solvent was distilled off under reduced pressure. The residue was shaken with 2 ml of trifluoroacetic acid at room temperature for 10 minutes and distilled under reduced pressure. The residue was dissolved in 5 ml of 5% acetic acid and the solution was passed through a column (1×10 cm) of Amberlite IRA-410(acetate-form). The effluent was concentrated under reduced pressure and the concentrate was run onto a column (2.3×118 cm) of Sephadex G-25, elution being carried out with 50% acetic acid. The fractions from 185 ml to 280 ml were pooled and lyophilized. Yield 93 mg; $[\alpha]_D^{26}$ −35.0° (c=0.3, 50% acetic acid); Rf$^3$ 0.61 (Avicel®); amino acid analysis: Arg. 2.33(2); Trp 0.93(1); Asp 3.34(3); Thr 0.95(1); Ser 0.83(1); Glu 2.17(2); Ala 1.00(1); Val 1.05(1); Met 1.00(1); Leu 0.93(1); Tyr 0.97(1); Phe 1.03(1) (peptide content 75%)

EXAMPLE 7

(1) Production of Z-Arg(MBS)-Arg(MBS)-Ala-OH

In 20 ml of TFA was dissolved 3.0 g of Z-Arg(MBS)-Arg(MBS)-Ala.OBu$^t$. The solution was shaken at room temperature for 40 minutes and the solvent was distilled off under reduced pressure. Ether was added to the residue and the resultant powders were collected by filtration and dried. The dried powders were purified by silica gel column chromatography (40 g silica gel:-developer solvent:chloroform-methanol-acetic acid=9:1:0.5), the resultant oil was treated with ether and the powders thus formed were collected by filtration. Yield 2.1 g (73.0%); m.p. 112°–115° C.; $[\alpha]_D^{21}$ −2.5° (c=1.1%, DMF);

Elemental analysis: calcd. for $C_{37}H_{49}O_{12}N_9S_2 \cdot H_2O$—C, 49.71; H, 5.75; N, 14.10; S, 7.17; found—C, 49.87; H, 5.87; N, 13.96; S, 6.76.

(2) Production of H-Arg-Arg-Ala-Gln-Asp-Phe-Val-Gln-Trp-Leu-Met-(O)-Asn-Thr-OH

To 800 mg of Boc-Gln-Asp(OBzl)-Phe-Val-Gln-Trp-Leu-Met(O)-Asn-Thr-OBzl was added 0.2 ml of anisole and, in nitrogen gas streams, 10 ml of TFA was added and the mixture was shaken at room temperature for 10 minutes. The TFA was distilled off under reduced pressure, the residue was treated with ether and the resultant powders were collected by filtration. The powders were dissolved in 5 ml of NMP and after the solution was neutralized with TEA, it was treated with ether. The resultant powders were collected by filtration and dissolved in 10 ml of DMF. To this was added 440 mg of Z-Arg(MBS)-Arg(MBS)-Ala-OH and the mixture was cooled with ice-NaCl, followed by addition of 180 mg of HONB and 160 mg of DCC. The mixture was stirred for 24 hours and the solvent was distilled off under reduced pressure. To the residue was added 50 ml of ethyl acetate and the resultant powders were collected by filtration and washed with aqueous acetonitrile. Yield 680 mg. A 500 mg portion of the product was taken and 0.2 ml of anisole and 5 ml of methanesulfonic acid were added. The mixture was shaken at room temperature for one hour and, then, 100 ml of ether was added, whereupon precipitates were formed. The ether was decanted off, the residue was dissolved in 10 ml of water and the solution was passed through a column (1×10 cm) of Amberlite IRA-410(acetate-form). The effluent was treated with 0.5 N-ammonia at 0° C. for 30 minutes and lyophilized. The lyophilisate was dissolved in 50 ml of water and run onto a column (2.4×15 cm) of CMC. By the linear gradient method, elution was carried out from water (500 ml) to 0.2 M-aqueous ammonium acetate (500 ml) and the fractions from 215 ml to 305 ml were pooled and lyophilized. Yield 50 mg; $[\alpha]_D^{21}$ −48.2° (c=0.5%, 0.1 N-HCl); Rf$^3$ 0.53 (Avicel®).

(3) Production of H-Arg-Arg-Ala-Gln-Asp-Phe-Val-Gln-Trp-Leu-Met-Asn-Thr-OH

In 3 ml of 5% thioglycolic acid-50% aqueous acetic acid was dissolved 30 mg of H-Arg-Arg-Ala-Gln-Asp-Phe-Val-Gln-Trp-Leu-Met(O)-Asn-Thr-OH and reduction was carried out at 45° C. for 24 hours. Then, the reaction mixture was run onto a column (2.4×122 cm) of Sephadex G-25 and elution was carried out with 30% aqueous acetic acid. The fractions from 180 ml to 250 ml were pooled and lyophilized. Yield 29 mg; $[\alpha]_D^{21}$ −41.9° (c=0.4%, 0.1 N-HCl); Rf$^3$ 0.55(Avicel®); amino acid analysis: Trp 0.69(1); Arg 2.25(2); Asp 2.13(2); Thr 0.97(1); Glu 2.16(2); Ala 1.00(1); Val 1.01(1); Met 0.97(1); Leu 1.01(1); Phe 1.05(1); (peptide content 78%)

(4) Production of Hpa-Arg-Arg-Ala-Gln-Asp-Phe-Val-Gln-Trp-Leu-Met-Asn-Thr-OH

In a mixture of 2 ml of DMF and 0.5 ml of water was dissolved 20 mg of H-Arg-Arg-Ala-Gln-Asp-Phe-Val-Gln-Trp-Leu-Met-Asn-Thr-OH, followed by addition of 7 mg of Hpa-ONB. The mixture was stirred for 15 hours and was run onto a column (2.3×118 cm) of Sephadex G-25, elution being carried out with 50% acetic acid. The fractions from 170 ml to 210 ml were pooled and lyophilized. Yield 18 mg; Rf$^3$ 0.61 (Avicel); amino acid analysis: Trp 0.75(1); Arg 2.16(2); Asp 2.23(2); Thr 1.02(1); Glu 2.00(2); Ala 1.02(1); Val 1.00(1); Met 0.98(1); Leu 1.11(1); Phe 1.03(1); (peptide content 76%).

EXAMPLE 8

(1) Production of Z-Arg(MBS)-Ala-OH

In 10 ml of TFA was dissolved 1.3 g of Z-Arg(MBS)-Ala-OBu$^t$ and the solution was shaken at room temperature for 40 minutes. The solvent was then distilled off under reduced pressure. To the residue was added 50 ml of ether and the resultant powders were collected by filtration. The powders were purified by silica gel chromatography (20 g silica gel; developer solvent=chloroform-methanol-acetic acid=9:1:0.5), the resultant oil was treated with ether and the powders thus obtained were collected by filtration. Yield 0.90 g (76.2%); m.p. 68°–70° C.; $[\alpha]_D^{21}$ +3.4° (c=0.8%, DMF);

Elemental analysis: calcd. for $C_{24}H_{31}O_8N_5S$—C, 52.45; H, 5.69; N, 12.74; S, 5.83; found—C, 52.05; H, 5.94; N, 12.53; S, 5.61.

(2) Production of H-Arg-Ala-Gln-Asp-Phe-Val-Gln-Trp-Leu-Met(O)-Asn-Thr-OH 450 mg of Boc-Gln-Asp(OBzl)-Phe-Val-Gln-Trp-Leu-Met(O)-Asn-Thr-OBzl was treated with TFA as in Example 7 and dissolved in 10 ml of DMF. To the solution was added 160 mg of Z-Arg-(MBS-Ala-OH and, under cooling with ice-NaCl, 104 mg of HONB and 90 mg of DCC were added and the mixture was stirred for 24 hours. The solvent was distilled off under reduced pressure, ethyl acetate was added to the residue and the resultant powders were collected by filtration and washed with aqueous acetonitrile. Yield 460 mg.

A 350 mg portion of this product was taken and shaken with 0.20 ml of anisole and 3 ml of methanesulfonic acid at room temperature for 1 hour. To this was added 100 ml of ether, whereby an oily precipitate was formed. The ether layer was discarded by decanting, the residue was dissolved in 20 ml of water and the solution was passed through an ion-exchange column (1×10 cm) of Amberlite IRA-410(acetate-form). The effluent was treated with 0.5 N aqueous ammonia at 0° C. for 30 minutes and lyophilized. To the lyophilisate was added 4 ml of 30% acetic acid and the mixture was run onto a column (3.4×57 cm) of Sephadex LH-20, elution being carried out with 30% acetic acid. The fractions from 200 ml to 250 ml were pooled and lyophilized. Yield 40 mg; $[\alpha]_D^{21}$ −42.1° (c=0.4%, 0.1 N HCl); Rf³ 0.59(Avicel ®)

(3) Production of H-Arg-Ala-Gln-Asp-Phe-Val-Gln-Trp-Leu-Met-Asn-Thr-OH

In 2.5 ml of 5% thioglycolic acid-50% aqueous acetic acid was dissolved 25 mg of H-Arg-Ala-Gln-Asp-Phe-Val-Gln-Trp-Leu-Met(O)-Asn-Thr-OH and reduction was carried out at 45° C. for 24 hours. The reaction mixture was run onto a column (3.4×57 cm) of Sephadex LH-20 and elution was carried out with 30% aqueous acetic acid. The fractions from 200 ml to 240 ml were pooled and lyophilized. Yield 20 mg; Rf³ 0.62 (Avicel ®); amino acid analysis: Trp 0.74(1); Arg 1.13(1); Asp 2.08(2); Thr 0.95(1); Glu 2.03(2); Ala 1.00(1); Val 0.98(1); Met 0.93(1); Leu 0.99(1); Phe 0.98(1) (peptide content 79%)

(4) Production of Hpa-Arg-Ala-Gln-Asp-Phe-Val-Gln-Trp-Leu-Met-Asn-Thr-OH

In a mixture of 2 ml of DMF and 0.5 ml of water was dissolved 15 mg of H-Arg-Ala-Gln-Asp-Phe-Val-Gln-Trp-Leu-Met-Asn-Thr-OH, followed by addition of 7 mg of Hpa-ONB. The mixture was stirred for 15 hours. The reaction mixture was run onto a column (2.3×118 cm) of Sephadex G-25 and elution was carried out with 50% acetic acid. The fractions from 175 ml to 205 ml were pooled and lyophilized. Yield 13 mg. Rf³ 0.68(Avicel ®); amino acid analysis: Trp 0.72(1); Arg 1.13(1); Asp 2.15(2); Thr 1.00(1); Glu 2.15(2); Ala 1.02 (1); Val 1.00(1); Met 0.95(1); Leu 0.98(1); Phe 0.98(1) (peptide content 76%)

EXAMPLE 9

(1) Production of H-Ala-Gln-Asp-Phe-Val-Gln-Trp-Leu-Met(O)-Asn-Thr-OH 800 mg of Boc-Gln-Asp(OBzl)-Phe-Val-Gln-Trp-Leu-Met(O)-Asn-Thr-OBzl was treated with TFA as in Example 7 and dissolved in 10 ml of DMF. To this solution was added Z-Ala-ONB (prepared from 120 mg of Z-Ala-OH, 100 mg of HONB and 110 mg of DCC) and the mixture was stirred for 24 hours. The solvent was distilled off under reduced pressure, ethyl acetate was added and the resultant powders were collected by filtration. Yield 760 mg. A 500 mg portion of this product was taken and 0.5 ml of anisole and 5 ml of methanesulfonic acid were added. The mixture was shaken at room temperature for one hour. To this was added 100 ml of ether, whereby an oily precipitate was produced. The ether layer was removed by decanting. The residue was dissolved in 30 ml of 50% aqueous acetic acid, the solution was passed through an ion-exchange column (1×100 cm) of Amberlite IRA 410 (acetate form) and the effluent was lyophilized. The lyophilisate was suspended in 10 ml of water, treated with 0.5 N-aqueous ammonia at 0° C. for 30 minutes and lyophilized. The lyophilisate was dissolved in 5 ml of 50% acetic acid and the solution was run onto a column (3.4×57 cm) of Sephadex LH-20, elution being carried out with 50% acetic acid. The fractions from 215 ml to 265 ml were pooled and lyophilized. Yield 55 mg; Rf³ 0.68 (Avicel ®)

(2) Production of H-Ala-Gln-Asp-Phe-Val-Gln-Trp-Leu-Met-Asn-Thr-OH

In 3.0 ml of 5% thioglycolic acid-50% aqueous acetic acid was dissolved 30 mg of H-Ala-Gln-Asp-Phe-Val-Gln-Trp-Leu-Met(O)-Asn-Thr-OH and reduction was carried out at 45° C. for 24 hours. The reaction mixture was run onto a column (3.4×57 cm) of Sephadex LH-20 and elution was carried out with 50% acetic acid. The fractions from 235 ml to 280 ml were pooled and lyophilized. Yield 23 mg; Rf³ 0.72(Avicel ®); amino acid analysis; Trp (0.76(1); Asp 2.15(2); Thr 0.93(1); Glu 2.15(2); Ala 0.97(1); Val 1.00(1); Met 0.92(1); Leu 1.02 (1); Phe 1.02(1) (peptide content 82%)

(3) Production of Hpa-Ala-Gln-Asp-Phe-Val-Gln-Trp-Leu-Met-Asn-Thr-OH

In a mixture of 2 ml of DMF and 0.5 ml of water was dissolved 20 mg of H-Ala-Gln-Asp-Phe-Val-Gln-Trp-Leu-Met-Asn-Thr-OH, followed by the addition of 0.1 ml of TEA. Then, 9 mg of Hpa-ONB was added. The mixture was stirred for 15 hours. The reaction mixture was run onto a column (2.3×118 cm) of Sephadex G-25 and elution was carried out with 50% acetic acid. The fractions from 160 ml to 185 ml were pooled and lyophilized. Yield 18 mg; Rf³ 0.79 (Avicel ®); amino acid analysis: Trp 0.73(1); Asp 2.05(2); Thr 0.94(1); Glu 2.13(2); Ala 1.00(1); Val 0.97(1); Met 0.90(1); Leu 0.99(1); Phe 1.00(1) (peptide content 81%)

EXAMPLE 10

(1) Production of Boc-Nle-Asn-Thr-OBzl

Boc-Asn-Thr-OBzl (3.1 g) was dissolved in TFA (30 ml), and the solution was allowed to stand at room temperature for 10 minutes, and the solvent was evaporated. The residue was triturated with ether to give powders, which were dissolved in DMF (30 ml) together with TEA (1.5 ml) and to this was added Boc-Nle-ONB which was prepared from Boc-Nle-OH (1.69 g), HONB (1.50 g) and DCC (1.73 g). The mixture was stirred at room temperature for 15 hours and the solvent was evaporated. The residue was triturated with water (50 ml) to give powders, which were collected by filtration and washed with ether. Yield 3.8 g (96.7%); m.p. 160°–163° C. $[\alpha]_D^{21.5}$ −13.6° (c=0.8, DMF); Rf¹ 0.58

Elemental analysis: calcd. for $C_{26}H_{40}O_8N_4$—C, 58.19; H, 7.51; N, 10.44; found—C, 58.40; H, 7.60; N, 10.37.

(2) Production of Boc-Leu-Nle-Asn-Thr-OBzl

Boc-Nle-Asn-Thr-OBzl (3.50 g) was treated with TFA (30 ml) and the solvent was evaporated. The residue was triturated with ether to give powders, which were dissolved in DMF (30 ml) together with TEA (1.2 ml). To this was added Boc-Leu-ONB which was prepared from Boc-Leu-OH (1.66 g), HONB (1.41 g) and DCC (1.63 g). The mixture was stirred at room temperature for 15 hours and the solvent was evaporated. The residue was triturated with water (50 ml) to give powders, which were collected by filtration and washed with ethyl acetate. Yield 3.60 g (83.8%); m.p. 200°–201° C. $[\alpha]_D^{21.5} -22.7°$ (c=0.8, DMF), $Rf^1$ 0.60

Elemental analysis: calcd. for $C_{32}H_{51}O_9N_5 \cdot \frac{1}{2}H_2O$—C, 58.34; H, 7.96; N, 10.63; found—C, 58.06; H, 7.99; N, 11.02.

(3) Production of Boc-Gln-Asp(OBzl)-Phe-Val-Gln-Trp-Leu-Nle-Asn-Thr-OBzl

Boc-Leu-Nle-Asn-Thr-OBzl (2.00 g) was treated with TFA (20 ml) and the TFA salt obtained was then converted to the corresponding free base with TEA (1.3 ml) in DMF, followed by precipitation with ether. The free base was dissolved in DMF (40 ml) together with Boc-Gln-Asp(OBzl)-Phe-Val-Gln-Trp-OH (3.00 g) and to this were added HONB (2.20 g) and DCC (1.27 g) at 0° C.

After the mixture was stirred for 48 hours, the solvent was evaporated and the residue was triturated with water (50 ml) to give powders, which were collected by filtration and washed well with aqueous acetonitrile. Yield 3.3 g m.p. 210°–214° C. (decomp.) $[\alpha]_D^{21.5} -11.8°$ (c=0.6, NMP) $Rf^3$ 0.66

Elemental analysis: calcd. for $C_{78}H_{106}O_{19}N_{14}$—C, 60.68; H, 6.92; N, 12.73; found—C, 60.92; H, 7.30; N, 12.76.

(4) Production of H-Asp-Ser-Arg-Arg-Ala-Gln-Asp-Phe-Val-Gln-Trp-Leu-Nle-Asn-Thr-OH ([Nle²⁷]glucagon(15–29))

Boc-Gln-Asp(OBzl)-Phe-Val-Gln-Trp-Leu-Nle-Asn-Thr-OBzl (3.0 g) was treated with TFA (25 ml) in the presence of ethanedithiol (0.2 ml) at room temperature for 10 minutes and the TFA salt obtained was then converted to the corresponding free base with TEA (0.8 ml) in NMP, which was followed by precipitation with ether.

The free base was dissolved in DMF (50 ml) together with Boc-Asp(OBzl)-Ser-Arg(MBS)-Arg(MBS)-Ala-OH (2.1 g) and to this were added HONB (0.71 g) and DCC (0.60 g) under cooling with ice-sodium chloride.

After the mixture was stirred for 24 hours, the DCU formed was filtered off and the filtrate was subjected to evaporation. The residue was triturated with ethylacetate to give powders, which were collected by filtration and washed with ethyl acetate. Yield 3.6 g.

The protected pentadecapeptide (1.0 g) thus obtained was dissolved in anhydrous hydrogen fluoride (10 ml) in the presence of anisole (1 ml) and the mixture was kept to stand at 0° C. for 60 minutes.

After evaporation of the solvent, the residue was dissolved in water (50 ml) and then washed with ether (50 ml×2). The solution was passed through a column (1×10 cm) of Amberlite IRA-410 (acetate form) and the passed solution and washings were combined and lyophilized. (Yield 700 mg)

The crude peptide was dissolved in 50% acetic acid (10 ml) and passed through a column (2.2×110 cm) of Sephadex LH-20, elution being carried out with 50% acetic acid. The fractions (125–180 ml) containing the desired product were combined and lyophilized (Yield 220 mg).

The powders obtained were dissolved in water and applied to a column (2.2×20 cm) of CMC, which was eluted with ammonium acetate buffer (gradient: 0.005 M/0.2 M=500 ml/500 ml). The fractions (265–440 ml) containing the pure product were combined and lyophilized. Yield 145 mg, $[\alpha]_D^{22} -30.9°$ (c=0.3, 50% acetic acid), $Rf^3$ 0.60 (Avicel). Amino acid analysis; Arg 2.11(2); Trp 0.97(1); Asp 3.40(3); Thr 0.93(1); Ser 0.83(1); Glu 2.10(2); Ala 1.00(1); Val 1.04(1); Leu 0.91(1); Phe 0.84(1); Nle 1.06(1), (peptide content 74%).

(5) Production of Hpa-Asp-Ser-Arg-Arg-Ala-Gln-Asp-Phe-Val-Gln-Trp-Leu-Nle-Asn-Thr-OH H-Asp-Ser-Arg-Arg-Ala-Gln-Asp-Phe-Val-Gln-Trp-Leu-Nle-Asn-Thr-OH (15 mg) was dissolved in a mixture of dimethylsulfoxide (0.2 ml), DMF (1 ml) and water (0.2 ml) and to this was added Hpa-ONB (5 mg). After the mixture was stirred at room temperature for 24 hours, the solvent was evaporated. The residue was dissolved in 50% acetic acid (0.5 ml) and passed through a column (1.2×92 cm) of Sephadex LH-20, which was eluted with 50% acetic acid. The fractions (35–42 ml) containing the pure product were pooled and lyophilized. Yield 12 mg, $[\alpha]_D^{24} -30.6°$ (c=0.3, 50% acetic acid), $Rf^3$ 0.70 (Avicel). Amino acid analysis: Arg 2.19(2); Trp 0.67(1); Asp 3.19(3); Thr 0.76(1); Ser 0.64(1); Glu 1.92(2); Ala 1.00(1); Val 0.90 (1); Leu 0.85(1); Phe 0.84(1); Nle 1.15(1), (peptide content 76%).

EXAMPLE 11

Production of peptide (II') (Either one or both of $R'_1$ and $R'_2$ are $^{131}I$; $R_3$ is $CH_2$; $R_4$ is Asp-Ser-Arg-Arg-Ala; $R_5$ is Met)

To 1.2 m Ci of Na¹³¹I was added 20 μl of 0.25 M-phosphate buffer (pH 7.5). To this was added a solution of 1.5 μg of Hpa-glucagon fragment (15–29) in 5 μl of phosphate buffer was added. This was further followed by the addition of a solution of 20 μg of Chloramine-T in 20 μl of phosphate buffer and the mixture was shaken at room temperature for 5–30 seconds. Then, a solution of 120 μg of sodium metabisulfite in 50 μl of phosphate buffer was promptly added to the mixture to terminate the reaction. Then, 0.1 ml of a solution of potassium iodide (10 mg/ml) was added and the reaction mixture was passed over Sephadex G-25(1×20 cm). Elution was carried out with 0.05 M Veronal buffer solution (pH 8.6) and the fractions from 11.5 ml to 14 ml were collected.

The reactivity of the resultant peptide (II') thus obtained according to this invention with antibodies specific to pancreatic glucagon (G-21A, G-42) is shown in FIG. 1 [K. Shima and P.P.Foa. Clin. Chim. Acta 22, 511(1968)]

G-21A is a PG-specific antibody which was prepared using glucagon, while G-42 is a PG-specific antibody prepared using glucagon fragment (15–29). With respect to both of these antibodies, the peptide (II') of this invention displays a reactivity similar to that of iodoglucagon. The above fact indicates that the peptide (II')

of this invention is fully able to take the place of iodoglucagon.

EXAMPLE 12

To 0.5 m Ci of Na$^{125}$I was added 25 µl of 0.4 M phosphate buffer (pH 7.3). To this was added a solution of 2.5 µg of Hpa-glucagon fragment (15-29) in 10 µl of phosphate buffer. This was further followed by the addition of solution of 3.6 µg of Chloramine T in 10 µl of 0.04 M phosphate buffer (pH 7.4) and the mixture was shaken at room temperature for 60 seconds.

Then a solution of 48 µg of sodium metabisulfite in 20 µl of phosphate buffer was promptly added to terminate the reaction.

Then 50 µl of 1% potassium iodide solution, 5 µl of 2 M TRIS solution and 500 µl of TRIS-HCl buffer (0.1 M TRIS, 0.1 M NaCl, 0.05% BSA, pH 8.6) were added and the reaction mixture was passed over QAE-Sephadex A25 (1×10 cm). Elutions was carried out with TRIS-HCl buffer mentioned above, and the fractions from 33 to 54 ml were collected. The peptide (II') of this invention displays a reactivity better than that obtained in Example 11.

EXAMPLE 13

All the reagents and the procedures are the same excet 0.36 µg of Chloramine T was used instead of 3.6 µg of Chloramine T in Example 12.

The reactivity of the resultant peptide (II') of this invention was better than that in Example 11.

EXAMPLE 14

All the reagents and the procedures are the same except 28.8 µg of Chloramine T was used instead of 3.6 µg of Chloramine T in Example 12.

The reactivity of the resultant peptide (II') of this invention was better than that in Example 11.

What is claimed is:

1. A peptide of the formula: H-Asp-Ser-Arg-Arg-Ala-Gln-Asp-Phe-Val-Gln-Trp-Leu-Met-Asn-Thr-OH.

2. A product obtained by conjugating a peptide of the formula: H-Asp-Ser-Arg-Arg-Ala-Gln-Asp-Phe-Val-Gln-Trp-Leu-Met-Asn-Thr-OH with bovine serum albumin by means of glutalaldehyde.

3. An antibody specifically reactive to pancreatic glucagon produced by administering to a mammalian animal a product obtained by conjugating a peptide of the formula: H-Asp-Ser-Arg-Arg-Ala-Gln-Asp-Phe-Val-Gln-Trp-Leu-Met-Asn-Thr-OH with bovine serum albumin by means of glutalaldehyde.

4. An antibody as claimed in claim 3, wherein a rabbit is employed as the mammalin animal.

* * * * *